United States Patent [19]

Grayzel

[11] 4,026,302
[45] May 31, 1977

[54] METHOD OF IMPLANTING A PERMANENT PACEMAKER BIPOLAR LEAD APPARATUS AND AN IMPLANTABLE PERMANENT PACEMAKER BIPOLAR LEAD APPARATUS

[76] Inventor: Joseph Grayzel, 262 Fountain Road, Englewood, N.J. 07631

[22] Filed: Apr. 30, 1975

[21] Appl. No.: 573,042

[52] U.S. Cl. .............................. 128/418; 128/419 P
[51] Int. Cl.² ............................................ A61N 1/04
[58] Field of Search ............... 128/404, 418, 419 P, 128/419 PG

[56] References Cited

UNITED STATES PATENTS

| | | | |
|---|---|---|---|
| 3,087,486 | 4/1963 | Kilpatrick | 128/419 P |
| 3,216,424 | 11/1965 | Chardack | 128/419 P |
| 3,478,746 | 11/1969 | Greatbatch | 128/419 P |
| 3,614,955 | 10/1971 | Mirowski et al. | 128/419 P |
| 3,749,101 | 7/1973 | Williamson | 128/419 P |
| 3,807,411 | 4/1974 | Harris et al. | 128/419 P |

*Primary Examiner*—William E. Kamm

[57] ABSTRACT

A method of implanting a permanent pacemaker bipolar lead apparatus comprising positioning a first electrode, connected to one pole of the pacemaker, in a chamber of the heart adjacent the interior surface of the heart muscle, and positioning a second electrode, connected to the other pole of the pacemaker, adjacent the exterior surface of the heart muscle so as to overlie the first electrode, so that upon operating the pacemaker substantially all electric current from the pacemaker flows through the heart muscle. An implantable bipolar lead apparatus for a permanent pacemaker comprising a negative electrode including a recess cavity in the forward end thereof, positionable in a chamber of the heart adjacent the interior surface of the heart muscle, a first conductive cable connected at one end to the negative electrode and connected at the other end to the negative pole of the pacemaker, a positive electrode comprising a plate portion for fixing to the body tissue and a penetrating shaft portion extending from the plate portion including a recess cavity in the end thereof, positionable adjacent the exterior surface of the heart muscle overlying the negative electrode, and a second conductive cable connected at one end to the positive electrode plate and connected at the other end to the positive pole of the pacemaker, operable so that upon operation of the pacemaker substantially all electric current from the pacemaker flows through the heart muscle.

14 Claims, 2 Drawing Figures

METHOD OF IMPLANTING A PERMANENT PACEMAKER BIPOLAR LEAD APPARATUS AND AN IMPLANTABLE PERMANENT PACEMAKER BIPOLAR LEAD APPARATUS

BACKGROUND OF THE INVENTION

This invention relates generally to a method of and apparatus for electrically stimulating a heartbeat. More specifically, this invention relates to a method of implanting a permanent pacemaker bipolar lead apparatus, and an implantable permanent pacemaker bipolar lead apparatus.

Heartbeat pacing devices used to electrically stimulate a heartbeat in order to restore or control the rate and rhythm thereof are known as pacemakers, which generate electrical pulses of appropriate strength and duration for heartbeat stimulation. Such pacemaker electrical pulses are then conducted to a point or region of the heart muscle by means of conductors and electrodes comprised of suitable material and configured to make electrical contact with and couple to the heart muscle; such a combination of conductor and electrode is known as a lead system.

One form of pacemaker and lead system combination is known as a permanent pacemaker, used for long-term therapy. In employing permanent pacemakers, the pacemaker and lead system are implanted in the patient's body.

The most common form of implantable lead for a permanent pacemaker is known as a cardiac catheter, which comprises a flexible tube containing a conductive cable and an electrode at or near its distal end. In implanting a catheter lead, the distal end of the cardiac catheter is extended into the body and positioned in one of the chambers of the heart, with the electrode positioned to bear against the inner surface of the heart muscle. A form of implantable catheter lead used previously comprised a bipolar configuration in which the pacemaker's negative and positive terminals were each connected to a separate insulated conductive cable in the catheter, and each cable terminated in an exposed electrode at or near the distal end of the catheter. In the preferred arrangement of such bipolar catheter lead, the negative electrode was at the very tip of the catheter making direct contact with the interior surface of the heart muscle, and the positive electrode was positioned approximately one or two centimeters back from the catheter tip; electric current flowed between these two electrodes through the heart muscle and/or the blood in the heart chamber in which the electrodes were positioned. Since the heart muscle was in front of the negative electrode at the tip of the catheter, whereas electric current was directed to flow back towards the positive electrode, a portion of the electric current flowing between the two electrodes did not pass through the heart muscle, but rather traveled through the blood alone and was therefor without stimulating effect. In view of such loss of stimulating current, a greater electrical output was required from the pacemaker in order to reach the minimum current for stimulating the heart muscle, and more power was required by the pacemaker than was necessary for stimulation alone. In order to overcome the undesireable overconsumption of power frequently occurring with bipolar configurations, a unipolar configuration of implantable catheter lead was developed in which only the negative electrode was in the catheter at the tip thereof, and a separate positive electrode was implanted a variable distance from the heart to provide for the passage of a greater percentage of the total stimulating current through the heart muscle by creating a flow pattern of electric stimulating current with more flow lines or streamlines directed through the heart muscle. The most common form of positive lead in such systems was a large metallic plate on one surface of the pacemaker. Such a unipolar configuration proved to be only a slight improvement over the bipolar configuration. The substantial distance from the heart to the pacemaker, particularly when the pacemaker was implanted above the level of the heart in the vicinity of the shoulder or neck, permitted a substantial flow of electric current away from the negative electrode thereby preventing it from reaching the heart muscle. Both the bipolar and unipolar configurations permit an electric current flow pattern which diverges from the negative electrode so that current density within the heart muscle is less than anticipated in view of the total current produced by the pacemaker; therefore, the stimulating capacity of an electrical pulse from the pacemaker, dependant upon the current density produced by the electrical pulse within the heart muscle, is substantially diminished in such devices.

SUMMARY OF THE INVENTION

In view of the above, it is among the objects of this invention to provide a method of implanting a permanent pacemaker bipolar lead apparatus, and an implantable bipolar lead apparatus for a permanent pacemaker, in which substantially all electric current is directed to flow from the pacemaker through the heart muscle, and in which current density through the heart muscle is maximized.

The above objects and others are achieved in this invention by means of a method of implanting a permanent pacemaker bipolar lead apparatus comprising positioning a first electrode, connected to one pole of the pacemaker, in a chamber of the heart adjacent the interior surface of the heart muscle, and positioning a second electrode, connected to the other pole of the pacemaker, adjacent the exterior surface of the heart muscle so as to overlie the first electrode, so that upon operating the pacemaker substantially all electric current from the pacemaker flows through the heart muscle. The above objects and others are further achieved in this invention by means of an implantable bipolar lead apparatus for a permanent pacemaker comprising a negative electrode including a recess cavity in the forward end thereof, positionable in a chamber of the heart adjacent the interior surface of the heart muscle, a first conductive cable connected at one end to the negative electrode and connected at the other end to the negative pole of the pacemaker, a positive electrode comprising a plate portion for fixing to the body tissue and a penetrating shaft portion extending from the plate portion including a recess cavity in the end thereof, positionable adjacent the exterior surface of the heart muscle overlying the negative electrode, and a second conductive cable connected at one end to the positive electrode plate and connected at the other end to the positive pole of the pacemaker, operable so that upon operation of the pacemaker substantially all electric current from the pacemaker flows through the heart muscle.

DESCRIPTION OF THE DRAWINGS

This invention is illustrated, by way of example, in the accompanying drawings, in which.

DESCRIPTION OF THE PREFERRED EMBODIMENT

Figure 1:
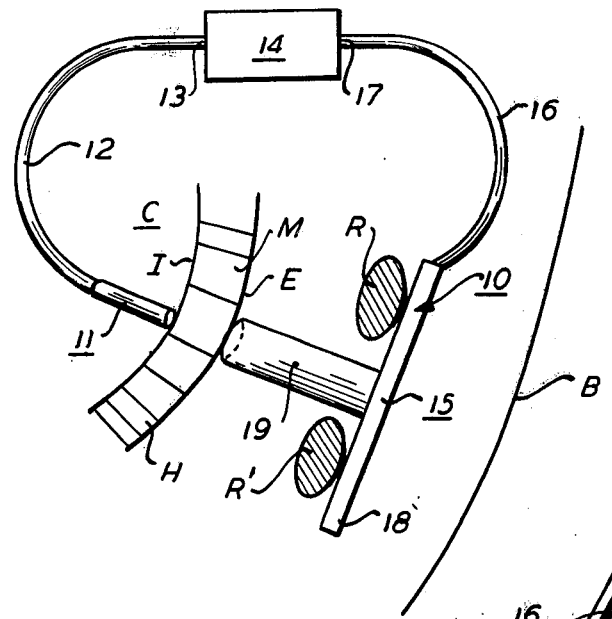
FIG. 1 is an elevational sectional view of a portion of the heart muscle and a portion of the chest with the permanent pacemaker bipolar lead apparatus implanted therein.
Figure 2:
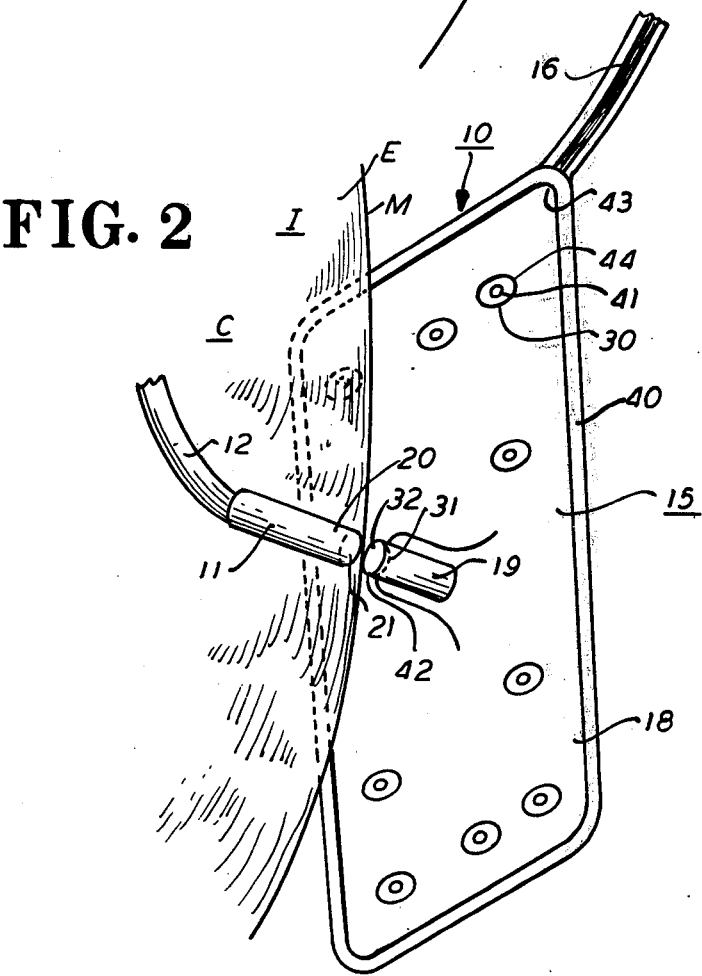
FIG. 2 is an elevational exploded view of the implantble permanent pacemaker bipolar apparatus.

In the preferred embodiment of the invention as lustrated in FIGS. 1 and 2, the method of implanting permanent pacemaker bipolar lead apparatus 10 in a atient's body B for electrically stimulating the paent's heart H comprises, for example, inserting a negive electrode 11, connected through first conductive ible 12 to the negative pole 13 of a pacemaker 14, rough the patient's venous channels into the ventricar chamber C to a position adjacent the inner surface of the ventricular muscle M of the patient's heart H, id inserting a positive electrode 15, connected rough second conductive cable 16 to the positive le 17 of the pacemaker 14, beneath the patient's skin id subcutaneous tissue into the intercostal space been the patient's ribs R, R' to a position which overs the portion of the ventricular muscle M beneath hich the negative electrode 11 is positioned, so that a ate portion 18 of the positive electrode 15 overlies e intercostal muscle and a penetrating shaft portion ' of the positive electrode 15 projects into the interior the chest cage to a position adjacent the exterior rface E of the ventricular muscle M so as to overlie e negative electrode 11, so that upon operating the cemaker 14 substantially all electric current from the cemaker 14 flows through the ventricular muscle M the heart H. Such positioning of the positive elec)de 15 further prevents twitching of the intercostal iscle. The second conductive cable 16 is inserted neath the patient's skin to extend along a path which erlies the path of extension of the first conductive ble 12, so as to minimize the electrical area of loop med by the lead system comprised of the negative nductor 11, first conductive cable 12, positive conctor 15, and second conductive cable 16, which nimizes the susceptibility of the apparatus to induced ltages from electromagnetic radiation in the environnt.

n the further preferred embodiment of the invention illustrated in FIGS. 1 and 2, the implantable permat pacemaker bipolar lead apparatus 10 comprises, example, the negative electrode 11 positionable in ventricular chamber C of the heart H adjacent the er surface I of the ventricular muscle M, the first iductive cable 12 connected at one end to the nega- electrode 11 and connected at the other end to the ative pole 13 of the pacemaker 14, the positive :trode 15 positionable adjacent the exterior surface f the ventricular muscle M so as to overlie the nega- electrode 11, and the second conductive cable 16 nected at one end to the positive electrode 15 and nected at the other end to the positive pole 17 of pacemaker 14. The negative electrode 11 includes mcave recess 20 in the end 21 thereof. The positive :trode 15 comprises the plate portion 18 comprised onductive material having openings 30 therein, the penetrating shaft portion 19 extending at substantially a right angle from the plate portion 18 including a concave recess 31 in the end 32 thereof and comprised of conductive material, a jacket 40 extending about the plate portion 18 and the penetrating shaft portion 19 and second conductive cable 16 comprised of insulating material compatable with body tissue such as a medical silicone rubber, having openings 41 therein communicating wit the openings 30 in the plate portion 18 and openings 42, 43 therein through which the end 32 of the penetrating shaft portion 19 and the second conductive cable 16 respectively extend, and reinforced eyelets 44, comprised of insulating material such as a biocompatible plastic, which extend through the openings 41 in the jacket 40 and the openings 30 in the plate portion 18 enabling suturing or fixation through such openings of the plate portion 18 of the positive electrode 15 to the surrounding body tissue for securing thereof. In operation, electric current from the pacemaker 14 flows through first conductive cable 12, negative electrode 13 and the concave recess 20 in the end 21 thereof, the ventricular muscle M of the heart H, the concave recess 31 in the end 32 of the penetrating shaft portion 19 and the penetrating shaft portion 19 and plate portion 18 of the positive electrode 17, and the second conductive cable 16. The path of electric current between the concave recess 20 in the end 21 of the negative electrode 11 and the concave recess 31 in the end 32 of the positive electrode 15 is substantially a short straight line through the thickness of the ventricular muscle M, following streamlines favoring maximum current density within the heart muscle, whereby substantially all electric current from the pacemaker flows through the heart muscle.

While this invention has been particularly set forth in terms of specific embodiments thereof, it will be understood in view of the present disclosure that numerous variations upon the invention are now enabled to those skilled in the art, which variations nevertheless are within the scope of the present teaching. Accordingly the invention is to be broadly construed, and limited only by the scope and spirit of the claims appended hereto.

I claim:

1. A method of implanting an apparatus for applying a pacemaker signal across the heart muscle, comprising:

a. positioning a first electrode, connected to a first pole of a pacemaker, in a chamber of a heart muscle adjacent the inner surface thereof; and b. positioning a second electrode, connected to the second pole of the pacemaker, subcutaneously and through the intercostal muscle to a position adjacent the outer surface of the heart muscle so as to overlie the first electrode, such that the signal from the pacemaker is applied intermediate the first and second electrodes through the heart muscle.

2. A method as in claim 1, in which the step of positioning the second electrode adjacent the outer surface of the heart muscle includes positioning a penetrating shaft portion of the second electrode so as to project into the interior of the thoracic cavity to a position adjacent the outer surface of the heart muscle.

3. A method as in claim 1, further comprising the step of positioning a second conductive cable, connecting the second electrode to the second pole of the pacemaker, so as to overlie the path of extension of a first conductive cable connecting the first electrode to the first pole of the pacemaker.

4. An apparatus for applying a pacemaking signal across the heart muscle, comprising:
   a. a first electrode connectable to a first pole of a pacemaker and positionable in a chamber of the heart muscle adjacent the inner surface thereof;
   b. a second electrode connectable to the second pole of the pacemaker and positionable subcutaneously and through the intercostal muscle to a position adjacent the outer surface of the heart muscle so as to overlie the first electrode.

5. An apparatus as in claim 4, in which the second electrode comprises a penetrating shaft portion comprised of conductive material.

6. An apparatus as in claim 5, in which the first electrode includes a concave recess in the distal end thereof, and the second electrode includes a concave recess in the distal end of the penetrating shaft portion thereof.

7. An apparatus as in claim 5, in which the second electrode includes a jacket extending thereabout, comprised of insulating material, having openings therein for connection thereto of an electrical connector from the second pole of the pacemaker and for extension therethrough of the distal end of the penetrating shaft portion.

8. An apparatus as in claim 5, in which the second electrode includes means for enabling the plate portion to be secured to the body tissue.

9. An apparatus as in claim 8, in which the enabling means comprises openings in the plate portion.

10. An apparatus as in claim 9, in which the enabling means further comprises reinforced eyelets positioned in the openings in the plate portion, comprised of insulating material.

11. An apparatus as in claim 5, in which the plate portion is comprised of a flexible material.

12. An apparatus as in claim 5, in which the penetrating shaft portion extends at substantially a right angle to the plate portion.

13. A method as in claim 2, in which the step of positioning the second electrode adjacent the outer surface of the heart muscle further includes positioning a plate portion of the second electrode so as to overlie the intercostal muscle.

14. An apparatus as in claim 5, in which the second electrode further includes a plate portion from which the shaft portion extends.

* * * * *